(12) United States Patent
Sperling et al.

(10) Patent No.: US 7,651,465 B1
(45) Date of Patent: Jan. 26, 2010

(54) METHODS AND APPARATUS FOR PERFORMING MINIMALLY INVASIVE SURGERY

(75) Inventors: Jason Scott Sperling, 23 Midland Dr., Upper Saddle River, NJ (US) 07458; Jeffrey A. Kinsberg, Matawan, NJ (US); Cristy J. Richards, Matawan, NJ (US)

(73) Assignee: Jason Scott Sperling, Upper Saddle River, NJ (US)

( * ) Notice: Subject to any disclaimer, the term of this patent is extended or adjusted under 35 U.S.C. 154(b) by 253 days.

(21) Appl. No.: 11/370,250

(22) Filed: Mar. 7, 2006

Related U.S. Application Data

(60) Provisional application No. 60/659,303, filed on Mar. 7, 2005.

(51) Int. Cl.
*A61B 1/32* (2006.01)
(52) U.S. Cl. .................................. 600/219; 600/231
(58) Field of Classification Search ......... 600/231–234, 600/201, 228, 235, 222, 230, 219, 227
See application file for complete search history.

(56) References Cited

U.S. PATENT DOCUMENTS

| | | | | |
|---|---|---|---|---|
| 810,675 | A * | 1/1906 | Richter | 600/219 |
| 4,300,541 | A * | 11/1981 | Burgin | 600/213 |
| 4,747,394 | A * | 5/1988 | Watanabe | 600/232 |
| 4,971,037 | A * | 11/1990 | Pelta | 600/234 |
| 4,989,587 | A * | 2/1991 | Farley | 600/228 |
| 5,067,477 | A * | 11/1991 | Santangelo | 600/222 |
| 5,088,472 | A | 2/1992 | Fakhrai | |
| RE34,150 | E | 12/1992 | Santilli et al. | |
| 5,616,117 | A * | 4/1997 | Dinkler et al. | 600/232 |
| 5,882,299 | A * | 3/1999 | Rastegar et al. | 600/232 |
| 5,967,972 | A * | 10/1999 | Santilli et al. | 600/232 |
| 5,984,867 | A | 11/1999 | Deckman et al. | |
| 6,099,468 | A * | 8/2000 | Santilli et al. | 600/232 |
| 6,224,545 | B1 | 5/2001 | Cocchia et al. | |
| 6,309,349 | B1 * | 10/2001 | Bertolero et al. | 600/213 |
| 6,322,500 | B1 * | 11/2001 | Sikora et al. | 600/219 |
| 6,821,247 | B2 | 11/2004 | Vierra et al. | |
| 2001/0018556 | A1 * | 8/2001 | Paolitto et al. | 600/232 |
| 2001/0041828 | A1 | 11/2001 | Deckman et al. | |
| 2002/0049369 | A1 | 4/2002 | Spence et al. | |
| 2002/0099269 | A1 | 7/2002 | Martin et al. | |
| 2002/0099272 | A1 | 7/2002 | Looney et al. | |
| 2004/0242968 | A1 | 12/2004 | Hill et al. | |

FOREIGN PATENT DOCUMENTS

WO    WO 98/27869    7/1998

\* cited by examiner

*Primary Examiner*—Eduardo C Robert
*Assistant Examiner*—Hao D Mai
(74) *Attorney, Agent, or Firm*—Lando & Anastasi, LLP

(57) ABSTRACT

A device for expanding an elongate opening formed in a skin layer of a patient includes a first arm for engaging one side of the opening and a second arm for engaging the other side of the opening. The device further includes a spreader mechanism, coupled to at least one of the first and second arms, to move the at least one of the first and second arms to widen the opening. The at least one arm is configured to move between a retracted position in which the at least one arm is positioned next to the other arm and an extended position in which the at least one arm is extended to expand the opening. Other embodiments of the device as well as methods for performing a medical procedure are further disclosed.

20 Claims, 15 Drawing Sheets

METHODS AND APPARATUS FOR PERFORMING MINIMALLY INVASIVE SURGERY

RELATED APPLICATIONS

This application claims priority under 35 U.S.C. § 119(e) to U.S. Provisional Application Ser. No. 60/659,303, entitled "METHODS AND APPARATUS FOR PERFORMING MINIMALLY INVASIVE SURGERY," filed on Mar. 7, 2005, which is herein incorporated by reference in its entirety.

BACKGROUND OF THE INVENTION

1. Field of the Invention

This invention relates generally to methods and devices for performing surgery, and more particularly, to methods and devices for performing minimally invasive surgery, such as cardiac surgery, including, but not limited to, coronary artery bypass grafting, valvular, dysrhythmia and aortic surgery, as well as thoracic surgical procedures.

2. Discussion of Related Art

Coronary artery disease is the largest or one of the largest causes of death in the United States. Interventions for coronary artery disease include education, medication, percutaneous coronary intervention, such as balloon angioplasty and stenting, and coronary bypass surgery.

Coronary artery bypass surgery is the most common type of heart surgery, with over 300,000 people having successful surgery in the United States each year. As is well known, arteries can become clogged over time by the build-up of fatty plaque in the artery wall. Coronary bypass surgery bypasses the diseased artery with a new blood vessel taken from the leg (greater saphenous vein) or an artery from the chest or arm. This procedure creates a new route for blood to flow.

Coronary artery bypass surgery is typically performed through an open chest exposure (i.e., to access and circumvent obstructed coronary arteries). A common approach involves making a 15-20 cm long incision in the skin overlying the breastbone, and splitting and separating the sternum to provide full access to the heart. With reference to FIG. 1, during coronary artery bypass surgery, the patient's breastbone 10 (sternum) is divided by means of a sternal saw. As stated above, a typical incision 12 is approximately 15-20 cm long. After appropriate bypass conduits are taken (e.g., a vein from the patient's leg), a sternal retractor is placed to spread the skin and breastbone to expose the heart and vessels for the bypass procedure. During the procedure, the heart may be stopped, and the patient's blood is sent through a heart-lung machine. This procedure typically takes three to five hours to perform, depending on the number of bypasses required. Three to four smaller incisions may be made inferior to the initial incision for drain placement around the heart after the procedure is completed. At the end of the procedure, the patient's breastbone is wired back together and the muscle and skin are closed as well with absorbable sutures.

The long incision 12 described above, which starts from the very top of the breastbone and extends the bottom of the breastbone, cuts not only the breastbone, but tissue and muscle as well. During the operation, a sternal retractor is situated above the cavity to spread the skin, tissue, muscle and breastbone. This large incision may cause several potential negative side effects. Of all the layers of body tissue, the skin is the most innervated with sensory nerves, as compared to muscle and breastbone. Further, closure of the pectoral muscles must be done in a fashion that results in much more tension on the muscles than the native state. This may result in extreme pain at rest which is exacerbated by any action that stretches the skin or muscle, which can lead to respiratory complications and general inactivity due to splinting. There may also be associated negative psychological effects.

Experience from other surgical procedures has shown that minimized surgical incisions result in shorter intensive care unit and hospital stays, less complications, less pain, and an overall better experience for the patient. For example, prior techniques in gallbladder removal (cholecystectomy) involved a substantial incision of 12-15 cm in the abdomen, which results in expected increased patient discomfort. When laparoscopic cholecystectomy was developed, which involves making four small incisions (each between 0.5 and 1.2 cm long) and the use of video equipment, the results was shorter hospital stays, less complications and quicker patient recovery.

Pecutaneous coronary intervention ("PCI") was developed as a less invasive way than coronary artery bypass grafting to treat coronary artery disease. PCI has progressed from balloon angioplasty, to stents, to drug eluting stents. However, PCI may not be suitable for patients who are diabetic or who have three or more artery blockages, according to the official recommendations of the American College of Cardiology.

Although there are examples of "minimal" invasive coronary artery bypass surgery, such surgery typically involves bypassing only left sided, anterior coronary vessels, through a limited rib spreading incision. This operation is only used for patients whose entire set of blockages can be bypassed through this smaller incision which represents a minority of patients.

Minimally invasive approaches to all types of operations are desirable because of the advantages of less scarring and pain, shorter hospital stays and recovery time. With minimally invasive approaches, such approaches generally try to avoid splitting the sternum and may use a series of incisions to gain adequate visualization and access the patient's heart. Rarely, with these approaches, is it possible to use videoscopic imaging systems or robotic guidance devices. While these techniques may provide advantages when dealing with a limited set of anatomic heart problems, they are not widely adopted due to their cumbersome nature, and the limited mobility through relatively fixed bony and muscular structures. There is concern that sub-par results may be obtained. In addition with small incisions, reduced three-dimensional visibility and perceptual orientation may increase some risk to the patient.

SUMMARY OF THE INVENTION

One aspect of the invention is directed to a method of performing coronary artery bypass and other open heart procedures. The method comprises: making at least one small incision of approximately 5 cm above the breastbone of the patient, with or without mobilizing the sternal envelope (fascia) in order to spare division of the pectoral muscles; dividing the entire breastbone to create an opening; inserting a device within the opening below the skin (and possibly, muscle) layer; expanding the device to increase the opening; performing a medical procedure; retracting the device; and closing the opening.

Another aspect of the invention is directed to a device for expanding an opening within a patient having a length of 5 cm or less. The device comprises a central body, and at least one arm coupled to the body. The arm is adapted to move between a retracted position in which the arm is housed within the central body and an extended position in which the arm is extended to expand the opening.

Yet another aspect of the invention is directed to a method of performing a medical procedure. The method comprises: making an incision in a patient; inserting a device through the incision and below a skin layer; expanding the device to expand an opening below the skin layer; and performing the medical procedure. In one embodiment, the opening is a division in the breastbone of a patient. The medical procedure may include pectoralis-sparing open heart surgery.

A further aspect of the invention is directed to a device for expanding an elongate opening formed in a skin layer of a patient, with the opening having opposite sides. The device comprises a first arm for engaging one side of the opening, a second arm for engaging the other side of the opening, and a spreader mechanism, coupled to at least one of the first and second arms, to move the at least one of the first and second arms to widen the opening. The at least one arm is adapted to move between a retracted position in which the at least one arm is positioned next to the other arm and an extended position in which the at least one arm is extended to expand the opening.

Embodiments of the device may further include the first and second arms comprising a distracter shaft and a support channel releasably secured to the distracter shaft. The support channel may be configured to engage a side of the opening. The support channel may further include a C-shaped surface adapted engage body tissue below the skin layer to widen the opening. The support channel may have a length of less than 5 cm. The support channel may have a wedge-shaped leading edge. In one embodiment, one of the first and second arms comprises an actuator member coupled to the spreader mechanism. The spreader mechanism comprises a gear box and a device for turning the gear box. The gear box comprises a first gear segment secured to the actuator member of the first arm and a gear wheel to engage the first and second gear segments. The gear box may further comprise a second gear segment secured to the actuator member of the second arm. A mount may be formed on the spreader mechanism, the mount being configured to secure the device to a support assembly. In another assembly, the spreader mechanism may comprise a scissor mechanism.

Another aspect of the invention is directed to a method of performing an open heart surgery procedure. The method comprises: making at least one small incision of approximately 5 cm above a breastbone of the patient; dividing the breastbone to create an opening; inserting a device within the opening below a skin layer; expanding the device to increase the opening; performing a medical procedure; retracting the device; and closing the opening. In one embodiment, the step of expanding the device includes moving at least one arm of the device to widen the opening.

Another aspect of the invention is directed to a device for expanding an elongate opening formed in a skin layer of a patient, with the opening having opposite sides. The device comprises a first arm for engaging one side of the opening and a second arm for engaging the other side of the opening. The first and second arms are configured to engage the sides of the opening below the skin layer. The device further comprises means for moving at least one of the first and second arms for widening the opening. The at least one arm is adapted to move between a retracted position in which the at least one arm is positioned next to the other arm and an extended position in which the at least one arm is extended to expand the opening. In one embodiment, the means for moving at least one of the first and second arms comprises a spreading mechanism disposed above the skin layer and coupled to the at least one of the first and second arms.

An additional aspect of the invention is directed to a method of performing a medical procedure. The method comprises: making an incision in a patient; inserting a device through the incision and below a skin layer; expanding the device to expand an opening below the skin layer; and performing the medical procedure. In one embodiment, the opening is a division in the breastbone of a patient. In another embodiment the medical procedure is pectoralis-sparing open heart surgery.

The present invention will be more fully understood after a review of the following drawing figures, detailed description and claims.

DESCRIPTION OF THE DRAWINGS

For a better understanding of the present invention, reference is made to the drawing figures which are incorporated herein by reference and in which.

DETAILED DESCRIPTION OF THE INVENTION

Figure 1:
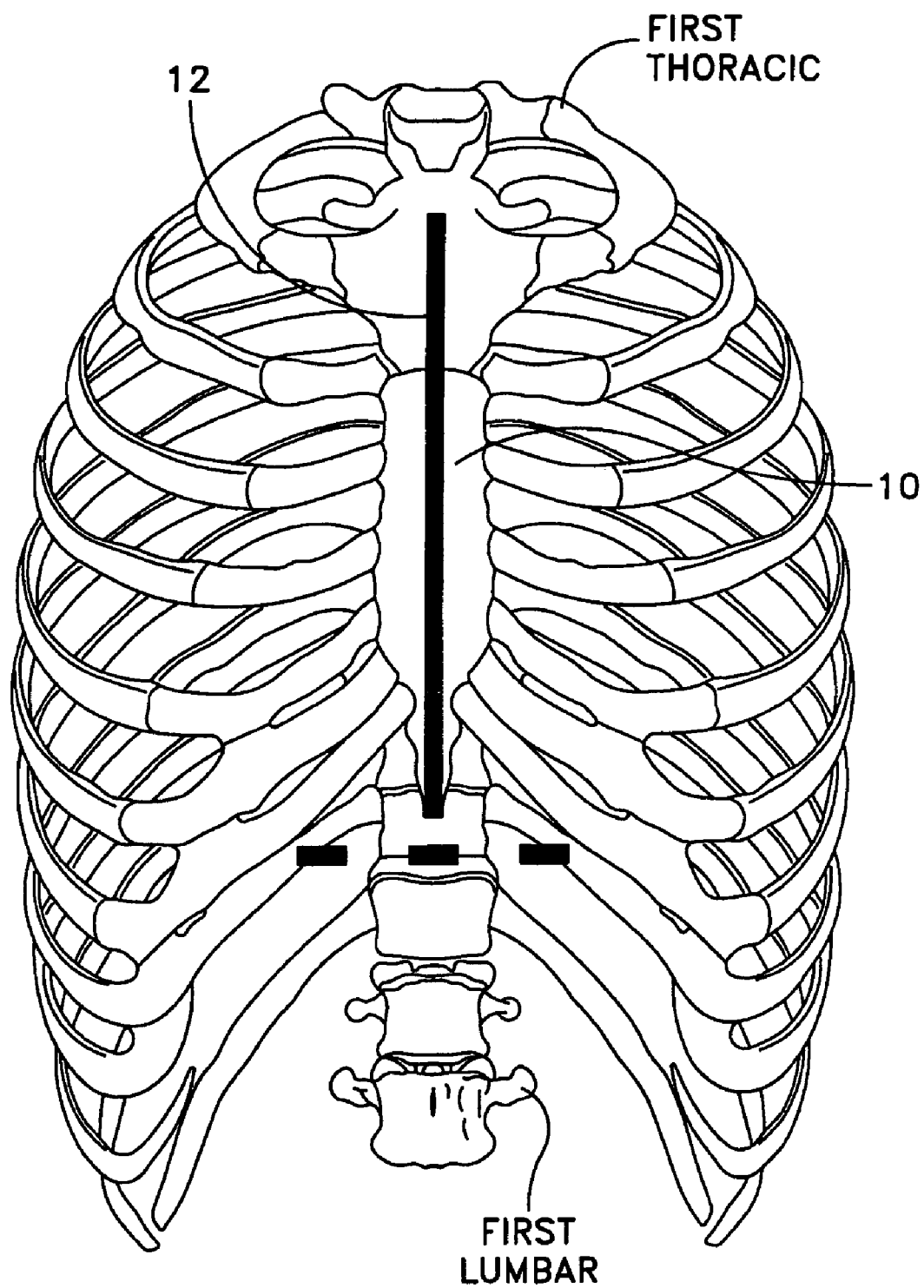
FIG. 1 is a representation of incisions made on a patient pursuant to a prior method of performing coronary artery surgery.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Generally, coronary artery bypass grafting procedures are performed one of two ways—beating heart surgery and non-beating heart surgery. The non-beating heart procedure uses a heart-lung cardiopulmonary bypass machine, in which the heart is purposely arrested (stopped) and the patient's blood is recycled and oxygenated by the machine. Beating heart surgery (also known as "off-pump" coronary bypass surgery) was performed before non-beating heart surgery and has recently been rejuvenated as a modern technique.

Figure 2:
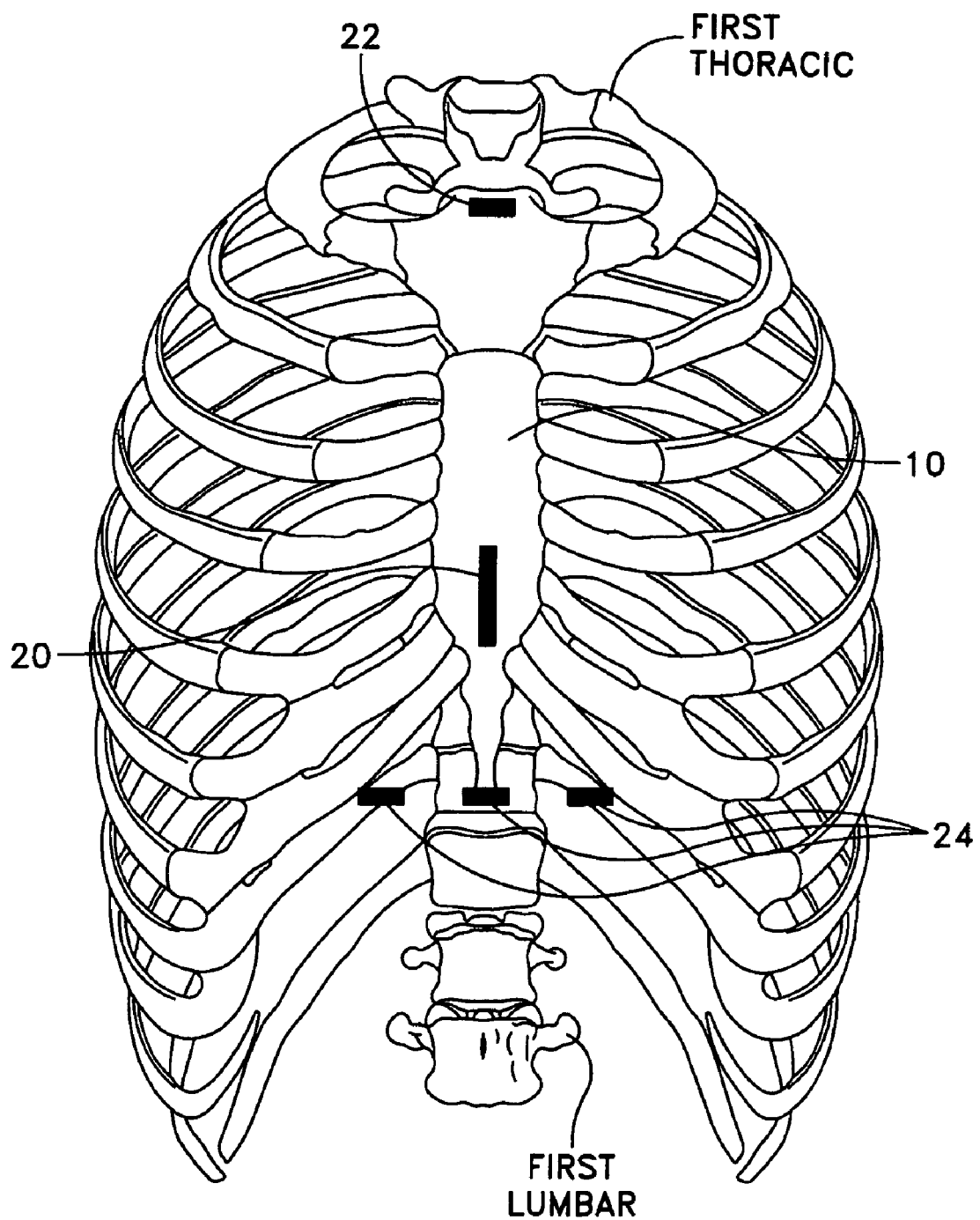
FIG. 2 is a representation of incisions made on a patient pursuant to a method of an embodiment of the invention for performing coronary artery surgery.

With reference to FIG. 2, a method according to one embodiment of the invention involves making a small incision, in an average size adult patient, of approximately 4-5 cm over the sternum and another cross incision of approximately 2 cm below the sternal notch. This method may be employed to perform pectoralis-sparing, minimally invasive coronary artery bypass surgery. As mentioned above, a first, vertically oriented small incision 20 is made in the lower third of the skin overlying the sternum, approximately 4-5 cm in length (the "working" incision). The first incision 20 is taken down to the level of the sternum 10 and the sternal envelope (investing fascia) is mobilized on the anterior surface using a combination of electrocautery and blunt dissection. The mobilization is carried out laterally with partial mobilization of the pectoralis muscle off of the chest wall. A second, horizontally oriented small incision 22 of approximately 2-3 cm horizontal is made just below the sternal notch (junction of the neck with the chest). This second incision 22 is used initially to help complete mobilization of the aforementioned tissues in the well-known manner. Once mobilization is complete, division of the sternum 10 is accomplished with a standard jigsaw using both incisions.

A mammary retractor may be used through the working incision 20 and below the skin to lift the left and/or right hemi-sternum in order to perform mammary artery pedicle harvesting using standard techniques, but through this small incision. For example, the mammary artery harvest may include adjunctive video assistance. Devices used to perform the method will be discussed in greater detail below with references to FIGS. 4-14.

Figure 3:
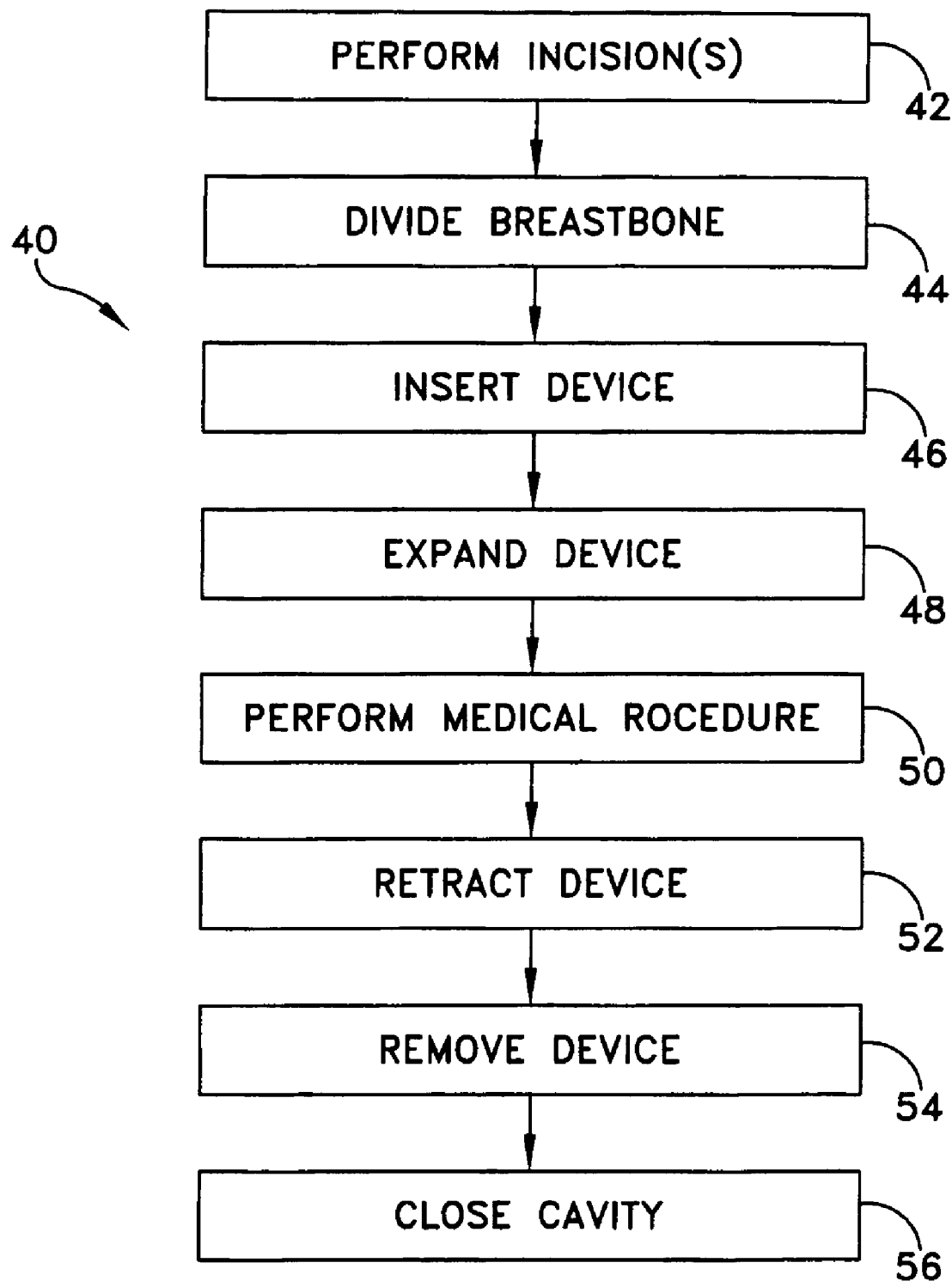
FIG. 3 is a block diagram showing a method of an embodiment of the invention for performing coronary artery surgery.

In an embodiment of a method of the invention, with reference to FIG. 3, a method of performing coronary artery bypass surgery, generally indicated at 40, is disclosed. A first small incision (e.g., 4-5 cm in length) is made to separate the patient's breastbone. A second small incision (e.g., 2 cm) is made horizontally just below the sternal notch. The incisions are indicated by step 42 in FIG. 3. Once mobilization is complete, the division of the sternum is achieved by standard techniques, e.g., by using a jigsaw (step 44).

A device, such as a retractor of embodiments of the present invention, is inserted into the cavity between the divided breastbone, as indicated by step 46 in FIG. 3. The device is manipulated below the skin layer to expand the opening to a distance sufficient to perform a medical procedure, such as coronary artery bypass surgery (step 48). In one embodiment, the breastbone may be expanded up to 20 cm.

Once opened, the medical procedure may be performed (step 50) via the opening. As disclosed herein, the retractor is especially suited for performing coronary artery bypass surgery. However, other procedures are contemplated, and may include, but are not limited to, bypass surgery, valvular and dysrhythmia surgeries and other procedures performed within the chest cavity. It should be understood that the methods and devices disclosed herein, may be applied to perform procedures at other locations within the body, e.g., the thorax or abdomen.

Once the procedure is performed, the device is retracted (step 52) and removed (step 54). At this point, the cavity defined by the opening may be appropriately closed (step 56) by wiring the breastbone and suturing the muscles and skin above the breastbone.

Figure 4A:
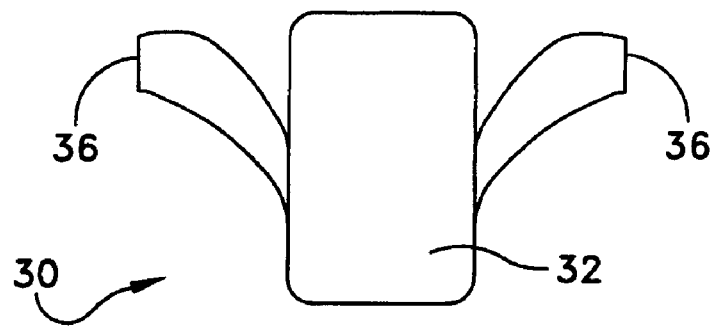
FIG. 4A is a schematic representation of a device of an embodiment of the invention for performing a method of coronary artery surgery, with arms of the device being shown in a retracted position.
Figure 4B:
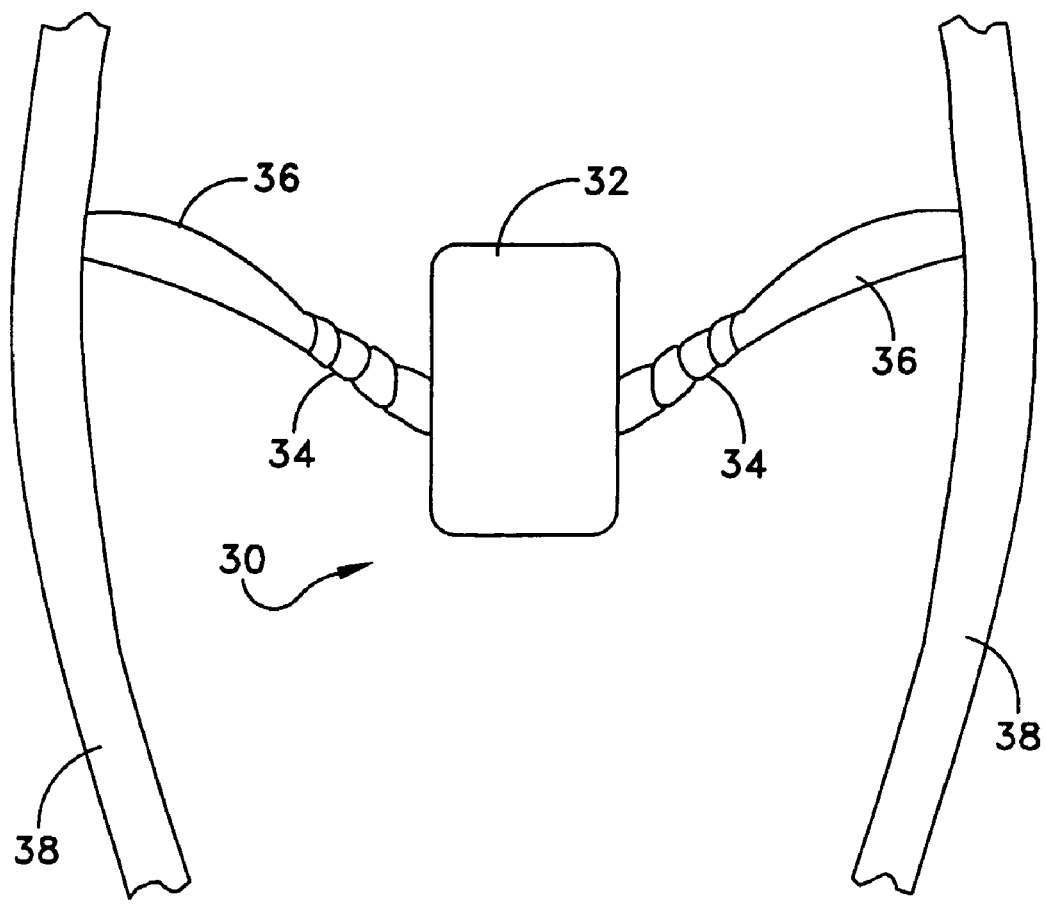
FIG. 4B is a schematic representation of the device shown in FIG. 4A, showing the arms of the device in an extended position.

With reference to FIGS. 4A and 4B, a retractor of an embodiment of the invention, generally indicated at 30, is designed so that its mechanism of retraction is under the level of the skin, as opposed to conventional retractors, which are typically placed on top of the sternum, and whose spreading mechanism is above the level of the dermis. A separate crank (not shown) may be placed through a different 1 cm stab incision 24 (FIG. 2) below the main working incision 20 to actuate the spreading mechanism. This stab incision 24 is in the location of one of the typical sites of chest drain placement after coronary artery bypass surgery, and may ultimately be utilized for such a drain. Three or four of these 1 cm stab incisions 24 may be made as illustrated to FIG. 2, all in positions of future drain sites. Once the sternum is spread to the standard width, the formal coronary artery bypass procedure is initiated.

The retractor 30 of an embodiment of the invention differs from prior retractors in its operable components are configured to be seated below the level of the dermis, mobilized pectoralis muscle, or the breastbone itself. The retractor 30 is capable of completely separating the breastbone as with prior retractors; however, the low profile of the retractor enables the retractor to be hidden away from the surgical field during the entire surgery.

As shown in FIGS. 4A and 4B, the retractor 30 comprises a central body 32 that may be generally rectangular, circular or oval in shape and sized to fit within the incision performed on the patient's breastbone. With reference to FIG. 4B, the central body 32 houses two telescopic arms, each arm indicated at 34, that extend outwardly from the central body. As shown, one arm 34 is positioned on one side of the central body 32 and the other arm is positioned on the other side of the central body. In another embodiment, a separate device may be provided, e.g., a frame, that houses the telescopic arms. Also, although two arms 34 are illustrated in FIG. 4B, the provision of a device having a central body that engages one side of the opening and one arm that engages the other side of the opening, or a device having more than two arms, e.g., four arms, is contemplated. Provided at the end of each telescopic arm is an end plate 36 that temporarily locks into a platform 38 adapted to conform to the sternal edges or sides of the patient's breastbone. Each platform 38 is approximately 5 cm long and is designed to cup the sternal edge in a longitudinal fashion. In this procedure, the central body 32 of the retractor 30 lies in a plane parallel to, but 1-2 cm below the lowermost plane of the platform 38. Upon extending the telescopic arms 34, the central body 32 is positioned 5-10 cm away from oppositely disposed platforms 38.

In an embodiment of the invention, the retractor 30 is adapted to slide into the incision between the divided breastbone. The central body 32 of the retractor 30 will lie below the plane of the sternum, but beyond the bottom of the heart towards the diaphragm, which separates the abdomen from the chest cavity. The dimensions of the central body 32, in one embodiment, may be 2 cm by 2 cm in area from top plan view and be rectangular, circular or oval in shape. Once in position, the sternum is separated by moving the telescopic arms 34 outwardly to engage the end plates 36 to their respective platforms 38. In one embodiment, the end plates 36 temporarily lock in place within grooves (not shown) formed in the platform 38. In this position, a medical procedure, such as cardiac surgery, may be performed. The minimal size of the retractor 30 enables the medical procedure to be performed.

The arrangement is such that when actuating the retractor 30 from above the skin incision, the telescopic arms 34 of the retractor extend and lock in place at a desired width of separation. The telescoping action of the arms 34 is designed to cause the upward angulation of the divided breastbone (up to 45° or more), which provides more volume under the incision for manipulation of the heart.

After the operation is complete, drains and pacing wires are placed. Afterwards, the telescopic arms 34 of the retractor 30 are retracted or withdrawn to within the central body 32 (FIG. 4A) and collapsed to its minimal size by a release mechanism (not shown) built into the central body of the retractor, and the retractor is removed from the patient.

In another embodiment, the device may include a two-part body having opposite edges arced or otherwise configured to engage opposite sides of the divided sternal edges. The device may be manipulated to pull the divided breastbone apart by, for example, a pair of wires that extends through lateral portions of the patient's chest cavity and is ratcheted to each side of the operating table.

In an embodiment of the invention, long needle drivers and forceps are used through the working incision. The thymus is divided and pericardium opened, and a pericardial well is created, using long needles that are passed through the skin and underlying muscle. Cannulation sutures are placed through the working incision while Rommel-type tourniquets are brought out through the upper counter incision. The aortic cannula is placed through the upper counter incision and cannulation itself is performed through the working incision. The tourniquets are tightened and the cannula is connected to the heart-lung machine. Venous cannulation is carried out using a long cannula through the common femoral vein in the groin, preferably using a percutaneous Seldinger technique or through the right chest into the atrium in the standard fashion. Cardiopulmonary bypass is established. A retrograde cardioplegia cannula and its tourniquet may be placed through one of the four 1 cm stab incisions (see FIG. 2), and the cannula placed through the working incision and positioned by digital palpation. An antegrade cardioplegia cannula, its tourniquet, as well as the aortic cross clamp may be placed through the upper counter incision. A left ventricular vent and its tourniquet can be placed through one of the stab incisions, and directed through the working incision. The aorta is dissected away from the pulmonary artery and aortic cross clamping/cardioplegia delivery is accomplished.

The heart is then mobilized to perform distal coronary anastomoses. The heart is moved, retracted, and stabilized using deep pericardial sutures or, e.g., sponge stick or other instruments that are brought in through the remaining stab incisions. Laparotomy pads may be delivered through the working incision and placed behind the heart to aid in mobilization. All coronary targets can be visualized through the working incision, and dissection and anastomoses may be carried out in the standard fashion. Once these are completed, proximal anastomoses are performed on the aorta in the usual way, either with the aortic cross clamp in place, or by replacing the cross clamp with a partial aortic clamp through the upper counter incision. Weaning from cardiopulmonary bypass and decannulation are completed. After hemostasis is ensured and drains are placed (and brought out through the stab incisions), the sternum is re-approximated with standard sternal wires through both the working and upper incisions. The upper and working incisions are closed with absorbable suture in layers.

As can be appreciated, the provision of smaller incisions results in improved aesthetics and less post-operative pain. Smaller incisions may significantly diminish the amount of pain associated with movement, ambulation, coughing and deep breathing. Smaller incisions may also lead to decreased atelectasis (lung segmental collapse) and pleural effusions, and other pulmonary complications. The aforementioned benefits would likely contribute to a shorter hospital stay and less reliance on health care benefits. Post-operative recovery may be significantly hastened, and resumption of full activity might be decreased to approximately 1-2 weeks from 4-6 weeks. Restrictions on activity may be lightened, because the pectoralis muscle complex has been mobilized off of the chest wall, and there will be significantly less force placed on the sternal (bone) closure. This may also potentially lead to a lower risk of sternal dehiscence (separation). As might be appreciated, based on the disclosure herein, some (but not all) embodiments of the present inventions can address or assist with respect to one or more of the above advantages.

Unknown beneficial attributes of the mesothelial cell lining of the heart and its associated tissues may be protected due to preservation of high levels of humidity because of the minimally invasive approach. Benefits may include less post-op adhesion formation (scarring) that would make re-operative cardiac surgery less risky. Similar benefits have been witnessed after laparoscopic and video-assisted thoracic surgeries. The prevention of desiccation (drying out) of these tissues may have a beneficial effect on the incidence of post-op atrial fibrillation (a heart rhythm disturbance that occurs in one-third of post-op cardiac patients and carries significant cost and morbidity). As might be appreciated based on the disclosure herein, some (but not all) embodiments of the present inventions can address or assist with respect to one or more of the above advantages.

Figure 5:
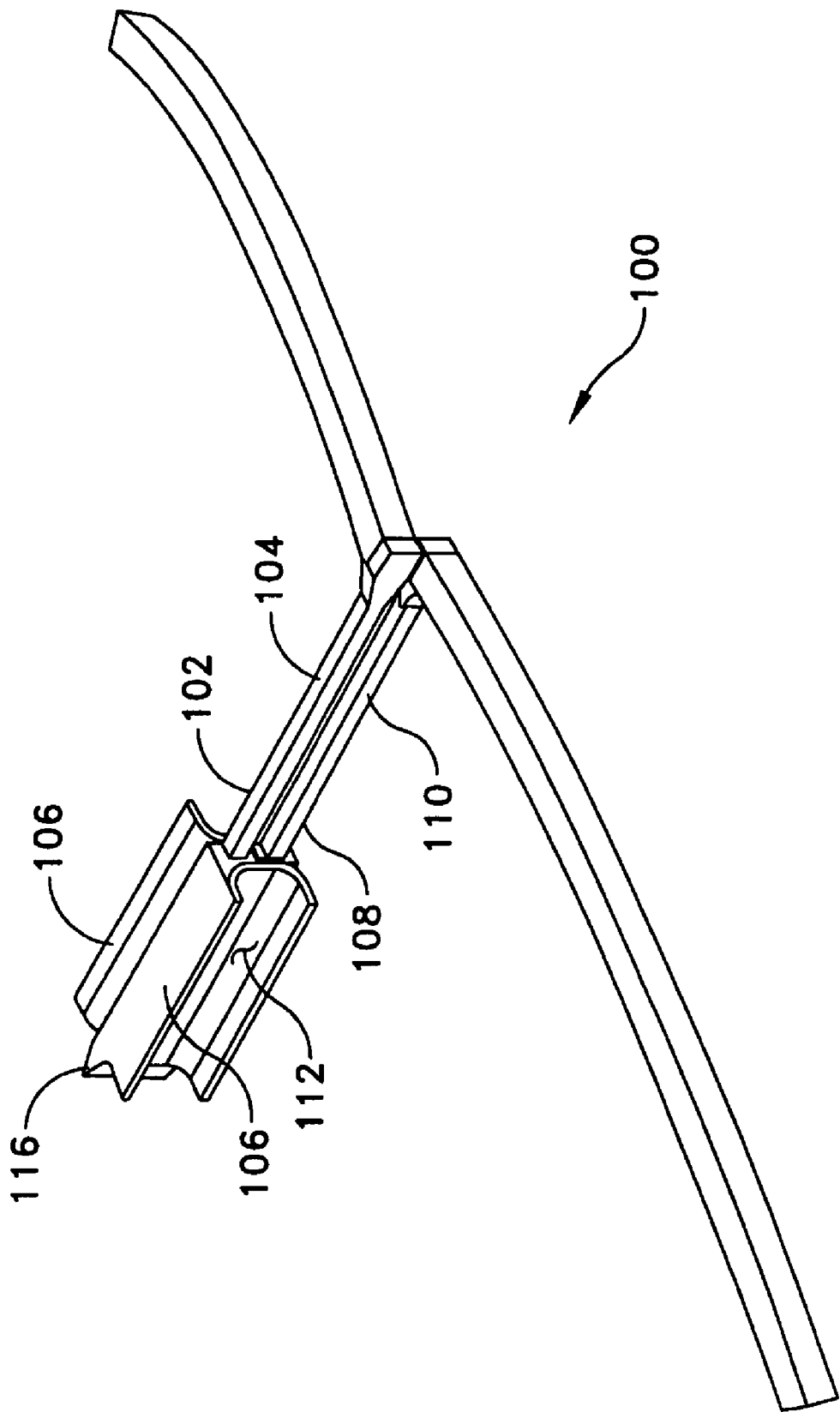
FIG. 5 is a perspective view of a device of another embodiment of the invention for performing a method of coronary artery surgery, with arms of the device being shown in a retracted position.
Figure 6:
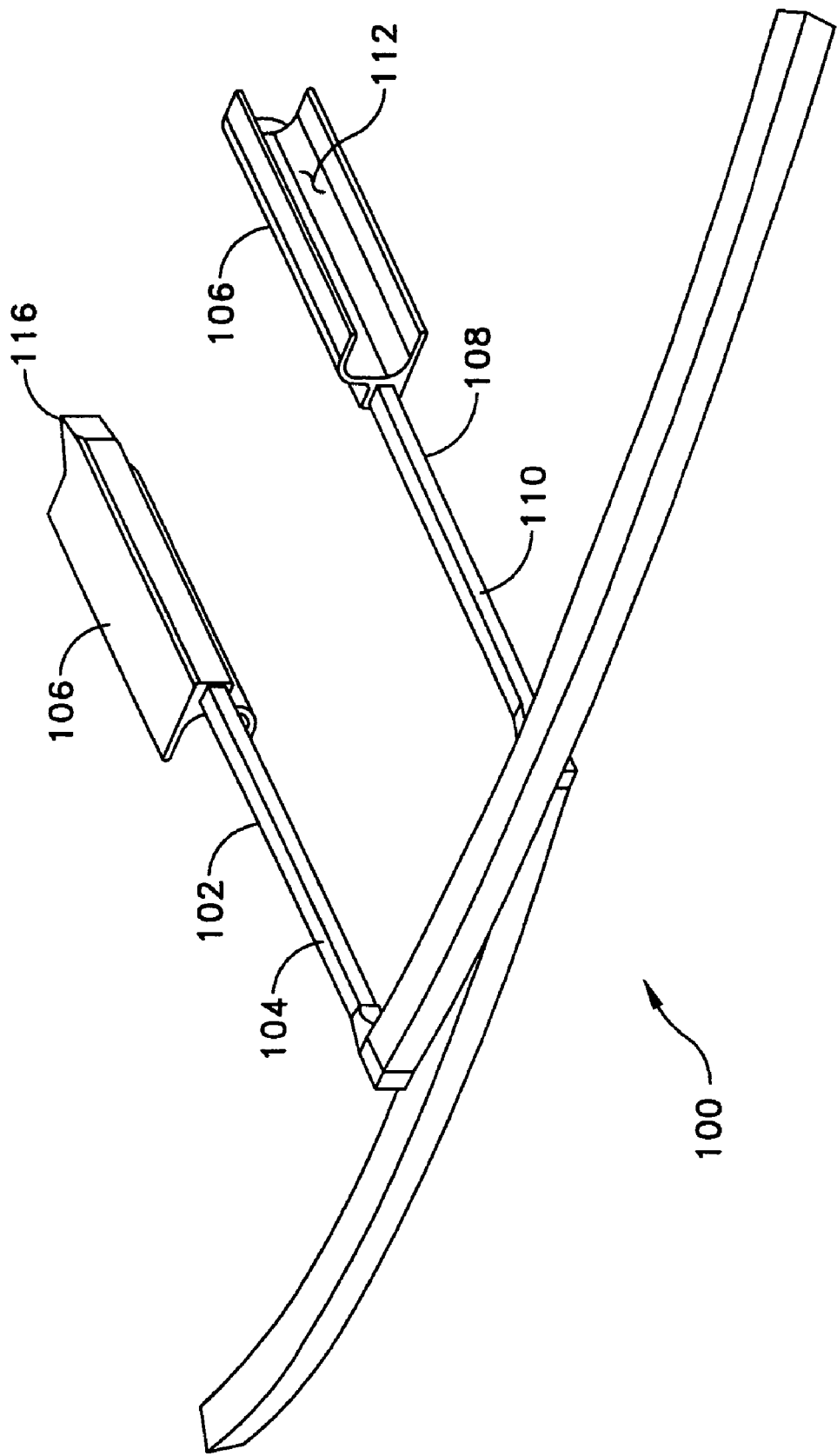
FIG. 6 is a perspective view of the device shown in FIG. 5, showing the arms of the device in an extended position.

Turning now to FIGS. 5 and 6, there is generally indicated at 100 a device of an embodiment of the invention for expanding an opening under the skin layer of a patient so that a medical procedure, such as cardiac bypass surgery, may be performed. As discussed above, the device 100 is configured to fit within and open a small incision (e.g., 4-5 cm in length) made to separate the patient's breastbone. The device may also be used to widen other openings formed in the patient, such as openings between the patient's ribs. The device includes a first arm 102 having a distracter shaft 104 and a support channel 106 that is releasably attachable to the distracter shaft 104. The device 100 further includes a second arm 108 having a distracter shaft 110 and another breastbone support channel 106 that is identical to the breastbone support channel 106 used on the first arm 102. The support channels 106 are configured to engage opposite sides of the opening of the patient (e.g., the left and right hemi-sternums). As shown in FIG. 5, the first and second arms 102, 108 may be positioned in a retracted position in which the arms are adjacent one another. In one embodiment, the first arm 102 may be configured to overly the second arm 108. FIG. 6 shows the first and second arms 102, 108 in an extended position so as to expand the opening by spreading the left and right hemi-sternums.

Figure 7:
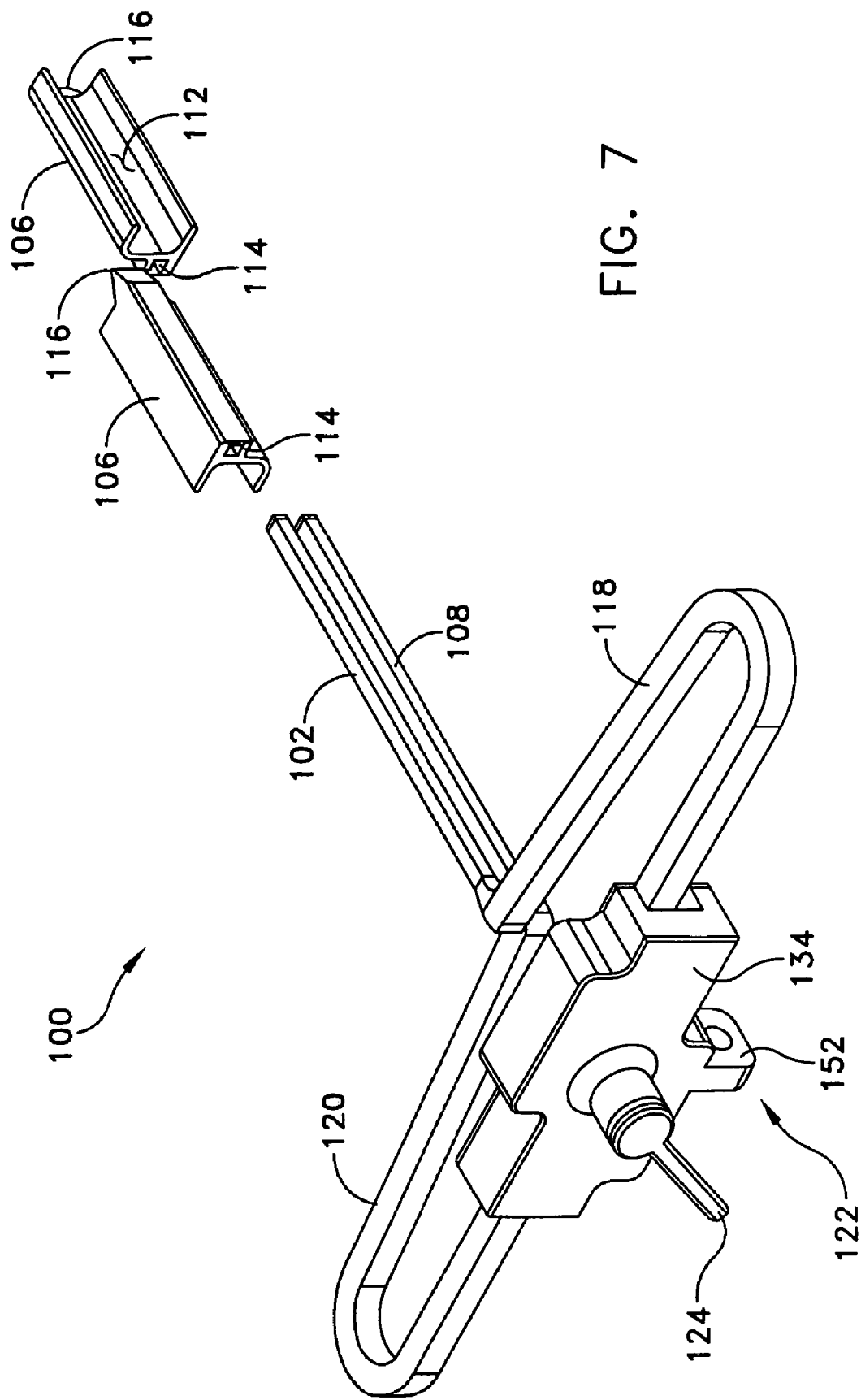
FIG. 7 is a perspective view of the device shown in FIGS. 5 and 6, with a operating mechanism being attached to actuating arms of the device and breastbone support channels being unattached to distracter shafts of the device.

In one embodiment, each support channel 106 includes a C-shaped surface 112 that is configured to engage the patient's divided breastbone under the skin layer. Although described to engage a patient's breastbone, the C-shaped surface 112 may be configured to engage other body tissue, such as a patient's rib. Referring to FIG. 7, each support channel includes an elongate opening 114 formed therein, and is attached to its respective arm 102 or 108 by sliding the distracter shaft 104 or 110 of the arm through the elongate opening. As shown, each support channel 106 includes a wedge-shaped leading edge or nose 116, which generates a dividing effect in distracting the breastbone. In a certain embodiment, the support channel 106 is approximately 5 cm long so as to fit within the opening of the patient.

Figure 8:
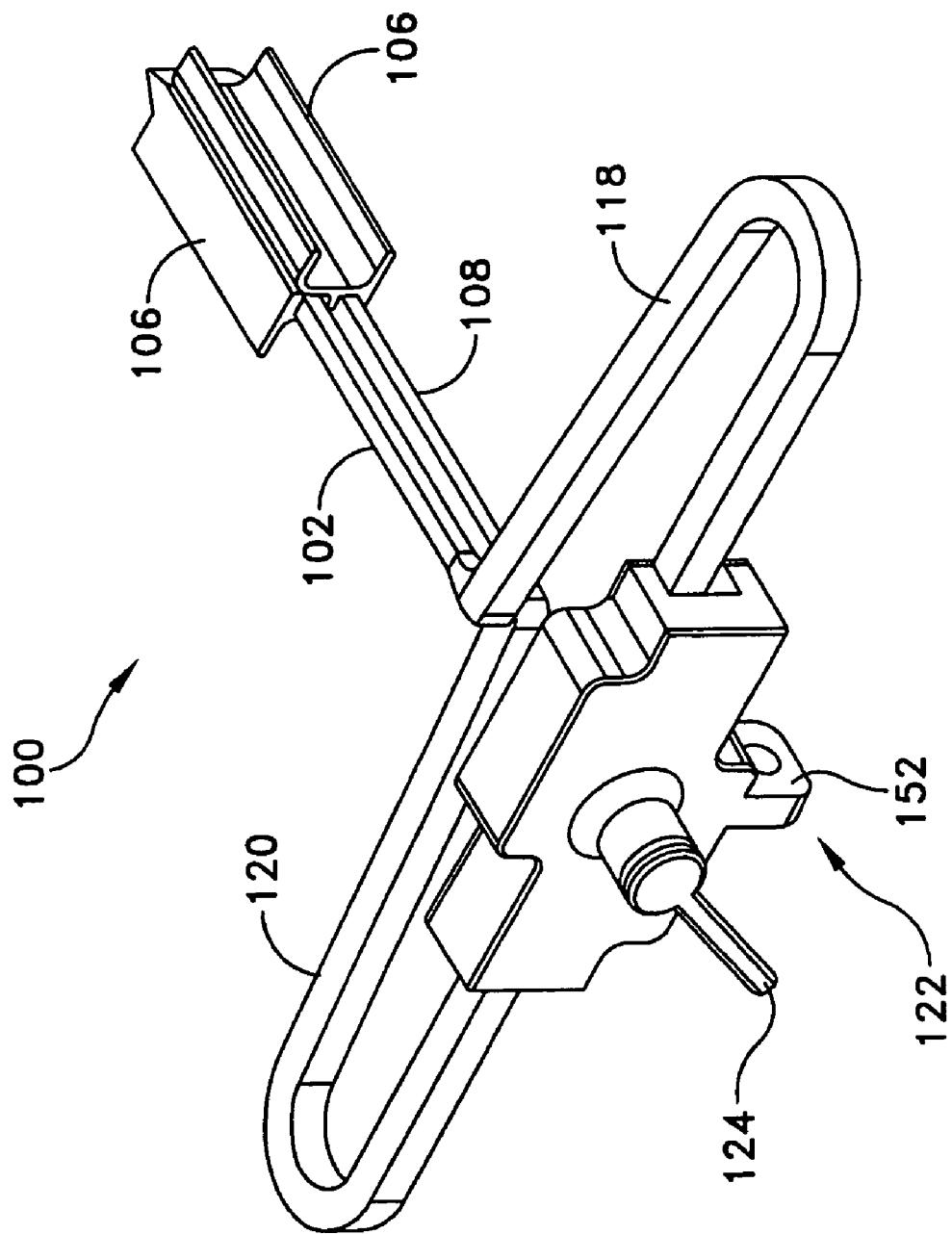
FIG. 8 is a perspective view of the device shown in FIG. 7, showing the breastbone support channels being attached to the distracter shafts and in a retracted position.
Figure 9:
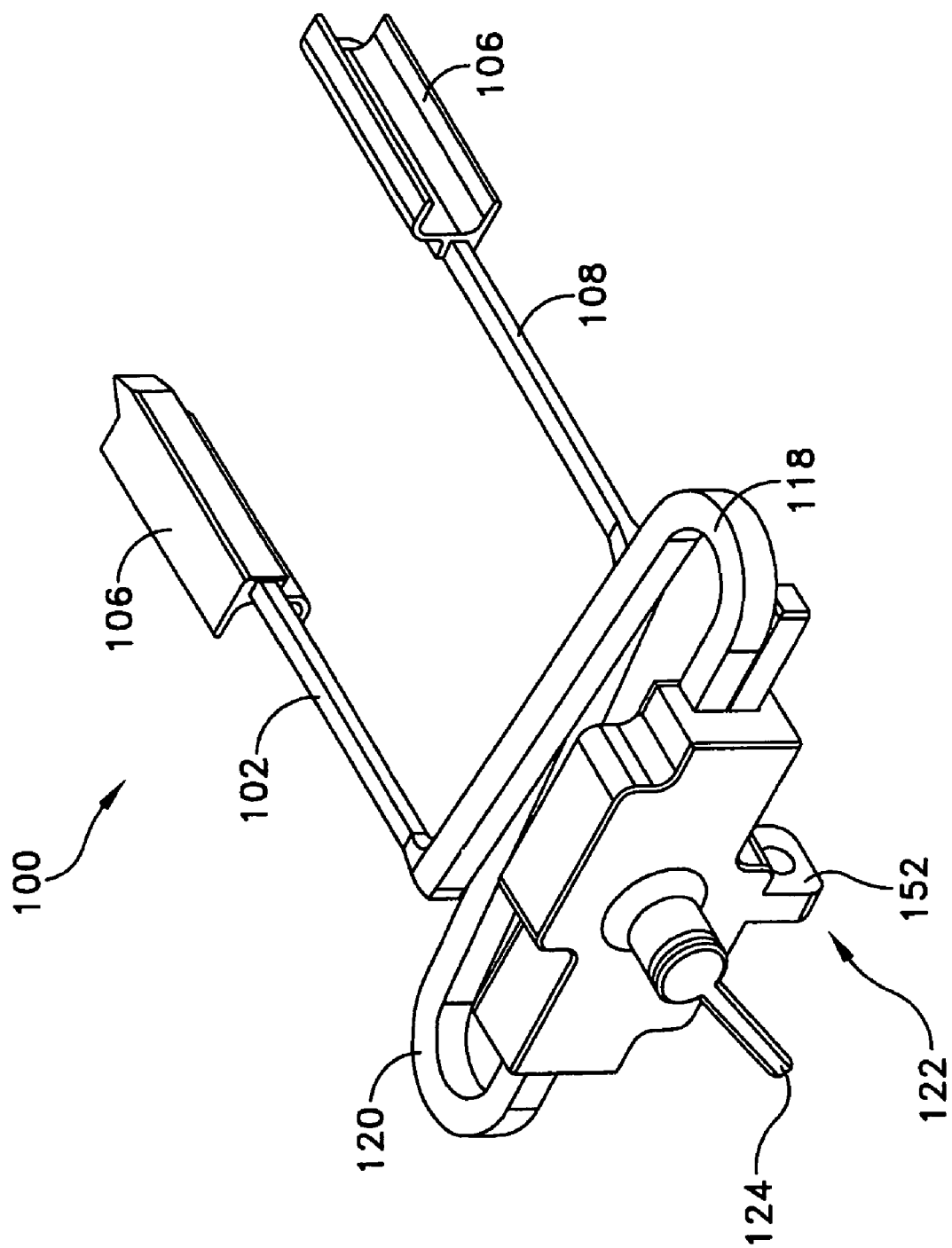
FIG. 9 is a perspective view of the device shown in FIG. 8, with the arms of the device being shown in an extended position.

Referring now to FIGS. 7-9, and more particularly to FIGS. 8 and 9, the first arm 102 is connected to a first actuator member 118 and the second arm 108 is connected to a second actuator member 120. Each actuator member 118, 120 is generally a U-shaped structure. The free ends of the actuator members 118, 120 are coupled to a spreader mechanism, generally indicated at 122, which is adapted to move the actuator members 118, 120 with respect to each other. Specifically, the spreader mechanism 122 is configured to move the first and second arms 102, 108 via respective actuator members 118, 120 between a retracted position in which the arms are positioned next to one another and an extended position in which the arms move away from each other. In other embodiments, the spreader mechanism 122 may be configured to move only one arm, e.g., first arm 102, with the other arm, e.g., second arm 108, being fixedly attached to the spreader mechanism. FIG. 8 shows the first and second arms 102, 108 in their retracted position. FIG. 9 shows the first and second arms 102, 108 in their extended position. A suitable device, such as a hand crank 124, may be provided to move the first and second arms 102, 108 between their retracted and extended positions. In other embodiments, an automated mechanism may be employed, such as a motorized system, to move the first and second arms 102, 108. In one embodiment, the extended position may widen the opening underneath the skin layer up to 20 cm, or more without tearing or otherwise harming the skin and muscle layers.

Figure 10:
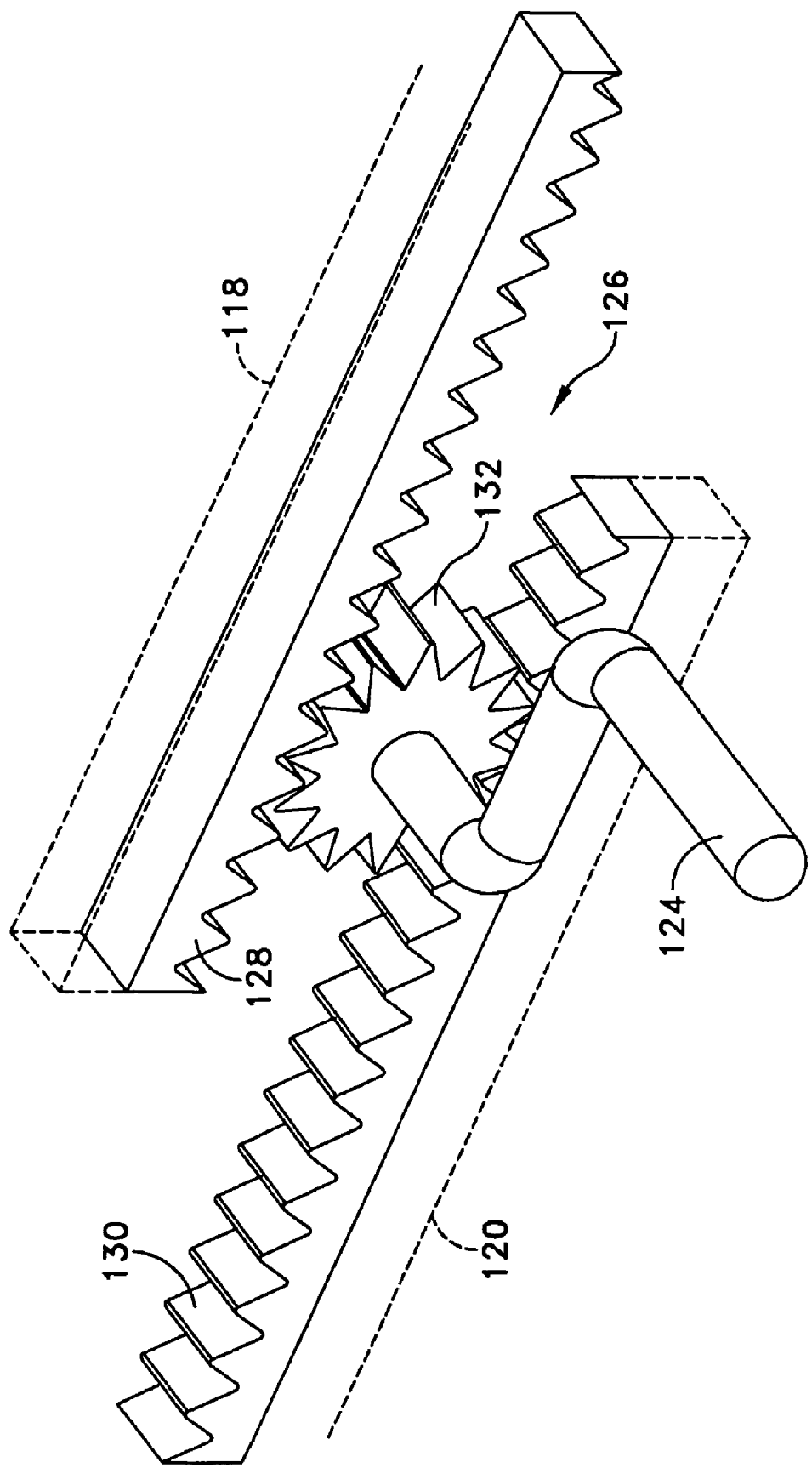
FIG. 10 is a perspective view of a gear box of the operating mechanism shown in FIGS. 7-9.

Turning now to FIG. 10, a gear mechanism, generally indicated at 126, is provided to move the first and second arms 102, 108 between their retracted and extended positions. As shown, the gear mechanism 126 includes a first gear segment 128 attached to the first actuator member 118. Similarly, a second gear segment 130 is attached to the second actuator member 120. A gear wheel 132 is suitably positioned between the first and second gear segments 128, 130. The gear wheel 132 is connected to the hand crank 124 so that upon rotating the hand crank, the gear wheel rotates. The arrangement is such that by rotating the hand crank 124, the first and second gear segments 128, 130 move the first and second actuator members 118, 120. With the arrangement illustrated in FIG. 10, by rotating the hand crank 124 in a clockwise direction, the first and second arms 102, 108 move to their retracted position. By rotating the hand crank 124 in a counterclockwise direction, the first and second arms 102, 108 move to their extended position. A suitable casing 134 (shown in FIGS. 7-9) is provided to house the components of the gear mechanism 126.

Figure 11:
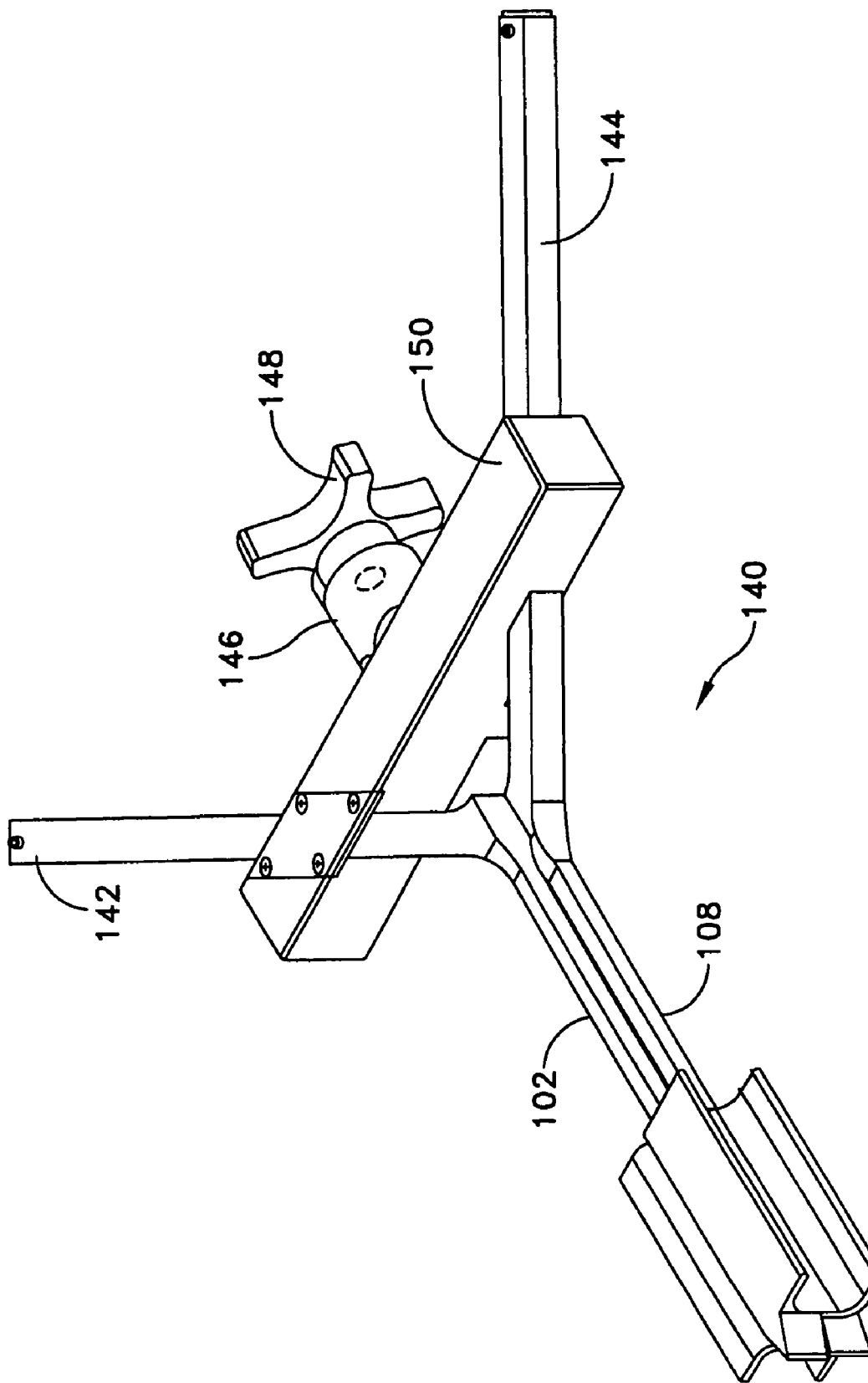
FIG. 11 is a perspective view a device of yet another embodiment of the invention for performing a method of coronary artery surgery, with arms of the device being shown in a retracted position.
Figure 12:
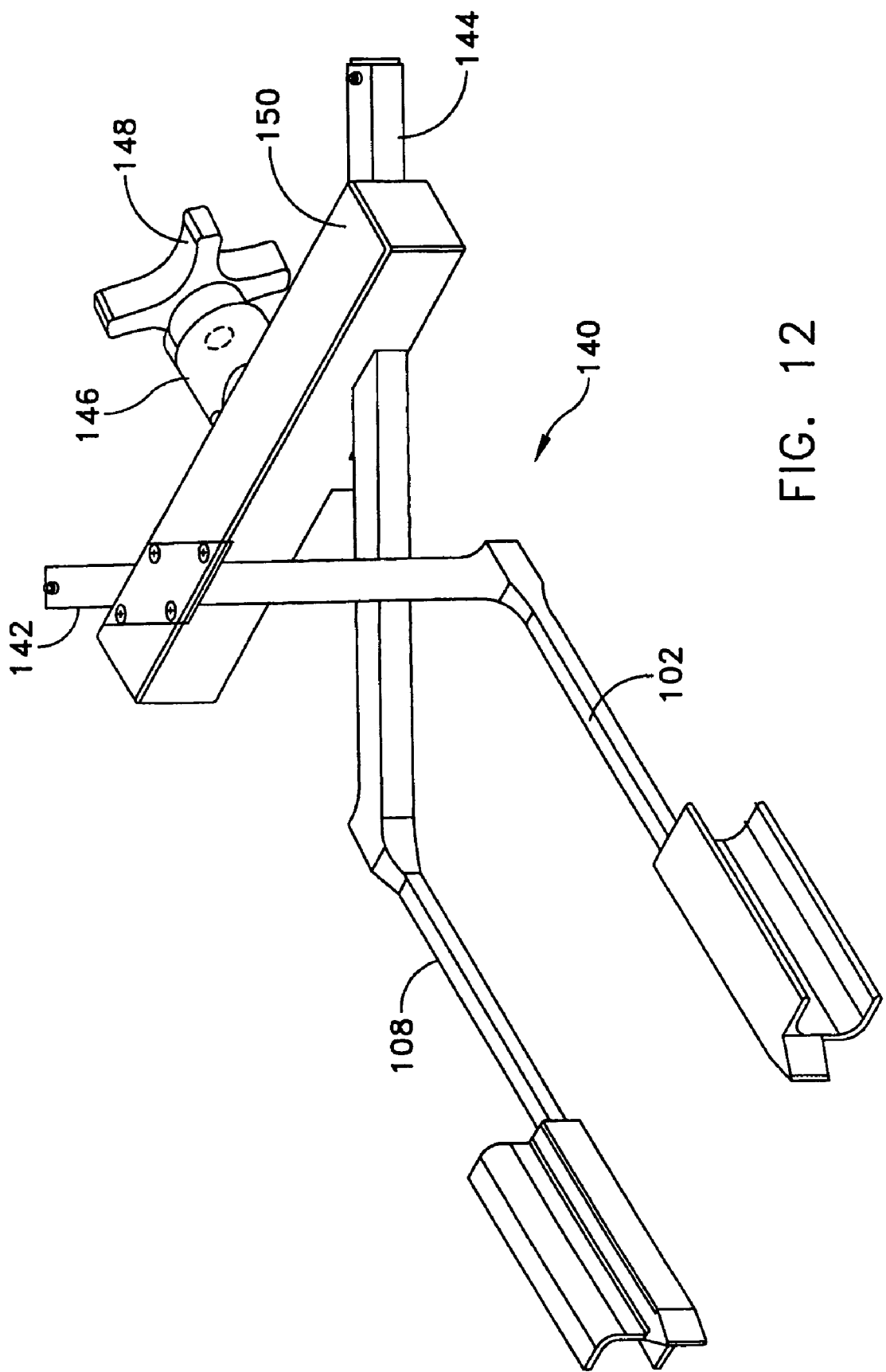
FIG. 12 is a perspective view of the device shown in FIG. 11, showing the arms of the device in an extended position

FIGS. 11 and 12 illustrate a device, generally indicated at 140, of another embodiment of the invention. As shown, the first and second arms 102, 108 of the device 140 are configured to be identical to the first and second arms 102, 108 of device 100. Device 140 includes straight actuator members 142, 144, that are connected to first and second arms 102, 108, respectively, and a spreader mechanism 146 designed to move the first and second arms 102, 108 via actuator members 142, 144 between retracted and extended positions. As shown, the spreader mechanism 146 is a scissor-type mechanism in which a knob 148 is provided to move the first and second arms 102, 108. FIG. 11 shows the first and second arms 102, 108 in their retracted position. FIG. 12 shows the first and second arms 102, 108 in their extended position to widen the opening. A casing 150 is provided to enclose the components of the spreading mechanism 146.

During use, a device, such as device 100 or 140, may be disposed over the patient so that the arms of the device are positioned underneath the patient's skin layer and the spreader mechanism is disposed above the patient. Since the spreader mechanism is located at one end of the device, the first and second arms, when moved to their extended position, enable the surgeon to view the cavity directly through the opening. A primary benefit of designing the support channels to engage tissue below the skin layer (e.g., the patient's breastbone) is that the incision can remain small (e.g., 5 cm). It is certainly contemplated, as witnessed by the embodiment of the device 30 shown in FIGS. 4A and 4B, the spreader mechanism (i.e., central body 32) may be disposed within the opening under the skin layer. However, the surgeon, when employing this type of device, must work around the spreader mechanism.

Figure 13:
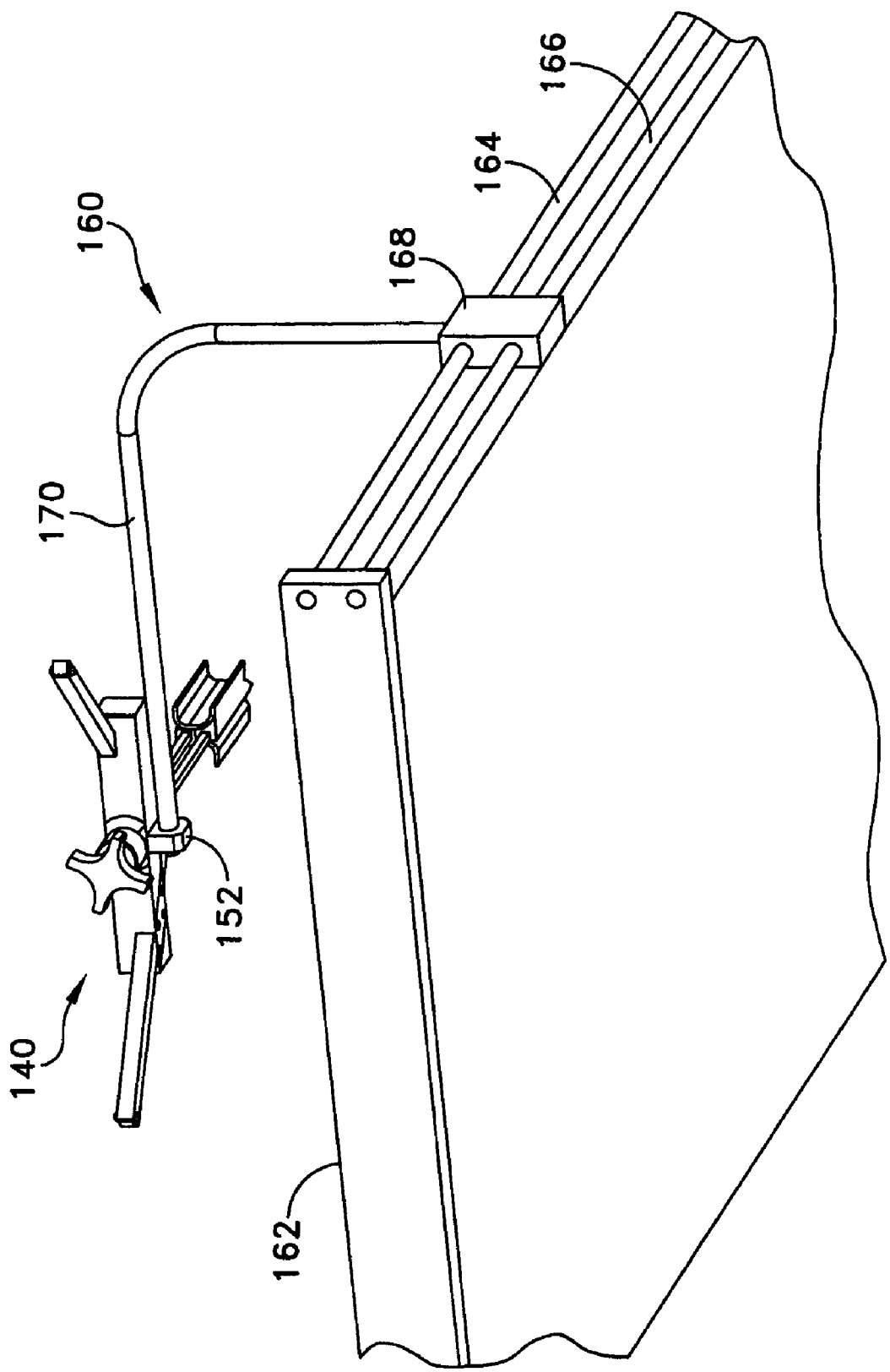
FIG. 13 is a bottom perspective view of the device shown in FIGS. 11 and 12 showing the device mounted on a support assembly.
Figure 14:
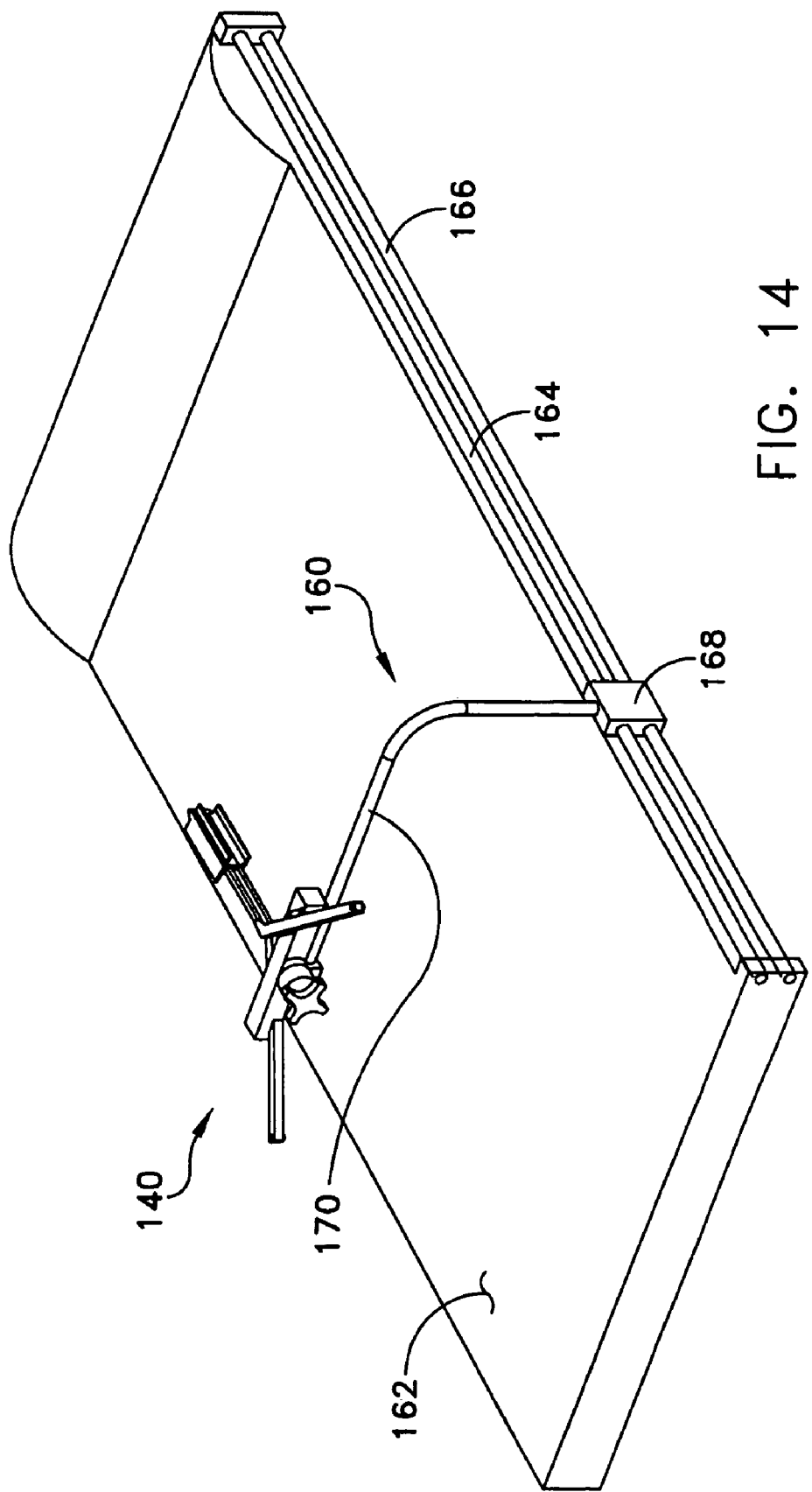
FIG. 14 is a top perspective view of the device shown in FIG. 13.

In one embodiment, the device 100 or 140 may include a mount 152 formed on the spreader mechanism 122 or 146 to mount the device on a support assembly. As shown, such a mount 152 is provided on the underside of the spreader mechanisms 122, 146. FIGS. 13 and 14 illustrate a support assembly, generally indicated at 160, that is integrally formed as part of an operating table 162. As shown, the operating table 162 includes a pair of rails 164, 166 and a slider 168 that is designed to slide along the lengths of the rails. A locking mechanism (not shown) may be provided to lock or otherwise secure the slider 168 in place. A support arm 170 is attached at one of its ends to the slider 168, the support arm 170 being configured to extend over the operating table 162 so that it is positioned above the patient. The other end of the support arm 170 is inserted into or otherwise connected to the mount 152 to secure the device 100 or 140 to the support arm. The arrangement is such that the device 100 or 140 may be slid along the length of the rails 164, 166 to position the device at any position over the patient. The support arm 170 may be telescopic, for example, so that the device 100 or 140 may be moved laterally with respect to the patient. Although FIGS. 13 and 14 illustrate the device 140, it should be understood, based on the foregoing description, that device 100 may be secured to the support arm 170 as well via mount 152.

Figure 15:
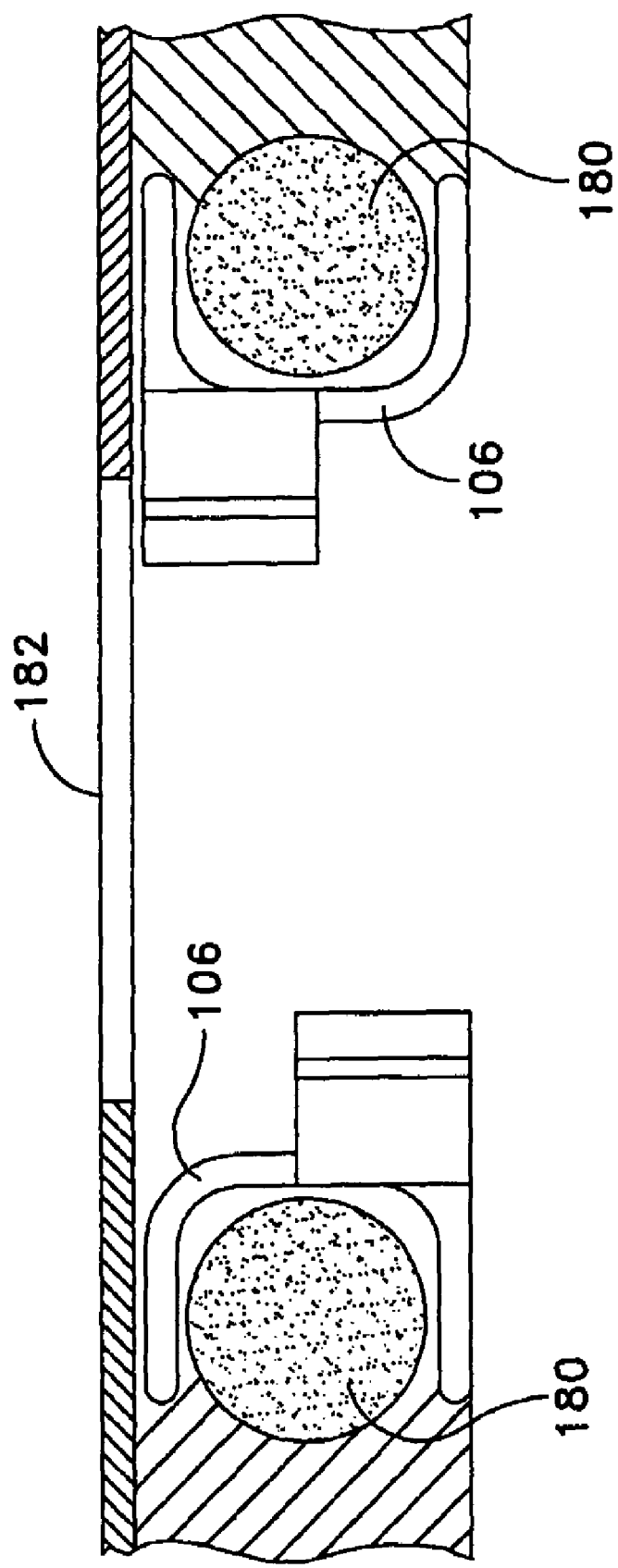
FIG. 15 is a cross-sectional view of a patient's breastbone being divided by a device of embodiments of the present invention.

In one application using the device, an access incision is created over the lower third of the breastbone longitudinally, and through it, tissues are dissected and the breastbone is completely divided with a standard jigsaw. As discussed, the device is modular in construction, and, in one embodiment, includes support channels with the C-shaped surfaces that are configured to contact and divide the breastbone. Reference may be made to FIG. 15, which illustrates the two support channels 106 engaging a divided breastbone 180 below the skin layer 182. In one embodiment, the support channels 106 are between 5 and 12 centimeters long. Two of these support channels, one for each hemi-sternum, are inserted into the access incision, and are directly applied to the split breastbone 180 longitudinally. As described with reference to devices 100 and 140, the remaining part of the device has long slender distracter shafts. With the device in the retracted, non-deployed position, the distracter shafts are inserted into a surgically created drain site or sites below the access incision and advanced to engage the two breastbone support channels. In this embodiment, the leading edges of these channels are pointed to allow for a wedge effect in distracting the breastbone 180. The distracter shafts are connected to the actuator arms, which, depending on the device, may be straight, curved, or of any other shape. The actuator arms are driven by the spreader mechanism that has a gear box provided in a casing or housing. The gear box in this example may be hand powered by a hand crank or a fluted thumb knob. In other embodiments, any suitable ergonomic device may be provided to allow the operator to distract the support channels with minimal effort. Integral with the casing of the spreader mechanism may be low friction guide shoes that allow either the actuation arms to pass through with low friction. There may be further provided assembly covers for the actuator arms to prevent trauma to the skin layer.

In certain embodiments, it is envisioned that the mount 152 may be adjunctively provided to enhance efficiency of the device. In one embodiment, the mount 152 affixes the device to the operating table 162 by securing the device to the support arm 170, which is slidably mounted on the operating room table by slider 168. This arrangement is designed to stabilize the device as the split breastbone 180 is distracted or separated. The mount 152 is designed to permit mobilization and fixation of the device at differing angles from its insertion angle. This configuration is intended to offset discrepancies in the angle at which the divided breastbone 180 is spread due to asymmetries in either the device or in the patient's body. In addition, the mount 152 may have further attachments to expand the device's capabilities to provide sites of fixation for stabilizing devices for beating heart surgery, or for hardware designed to distract the access incision to place it over different areas of interest and facilitate surgery, for example.

It is envisioned that a fiber optic carrier (e.g., cabling) may be incorporated into the actuator arms, and contiguously through the distracter shafts so that they may engage a light delivery system built into the breastbone support channels. This construction enables the surgical field to be lit from within opening, as opposed to directing light from outside the incision towards the deeper surgical field.

Similarly, video channeling or cabling may be built into the same above structures, with a video camera built into one or both the breastbone support channels to allow for live video of the surgical field for assistance during surgery or for recording and editing purposes. It this example, hardware for both light and/or video probes would attach to an appropriate portion of the actuation arms from a source off of the operating room table, as is done commonly for standard videoscopic procedures. In an alternate embodiment, the light and video optic cable could be connected to the breastbone support channels directly (without channeling through the actuator arms and distracter shafts, possibly through a one of the drain site incisions or another separate counter-incision.

In addition, separate hollow channels bored contiguously through the actuation arms and distracter shafts could be used for delivering sterile gas, such as carbon dioxide ($CO_2$), deep into the surgical field from a source off of the operating table, for example. $CO_2$ may be used in open heart surgery to displace air, as $CO_2$ is readily absorbed in blood, and air can cause "gas embolism," with undesirable consequences. Directed blasts of $CO_2$ can also be used to displace blood from surgical areas of interest during coronary surgery, for example.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A device for expanding an opening formed below a skin layer of a patient, the opening having opposite sides, the device comprising:
   a first arm for engaging a first side of the opening;
   a second arm for engaging a second side of the opening;
   a first generally U-shaped actuator member having one end connected to the first arm and an opposite end;
   a second generally U-shaped actuator member having one end connected to the second arm and an opposite end; and
   a single spreader mechanism, coupled to the first and second generally U-shaped actuator members at the opposite ends of the first and second generally U-shaped actuator members, to move the first and second arms to widen the opening below the skin layer, wherein the arms are adapted to move between a retracted position in which one arm is positioned next to the other arm and an extended position in which the arms are extended to expand the opening.

2. The device of claim 1, wherein each of the first and second arms comprises a distracter shaft and a support channel releasably secured to the distracter shaft, the support channel being configured to engage a side of the opening.

3. The device of claim 2, wherein the support channel includes a C-shaped surface adapted to engage body tissue below the skin layer to widen the opening.

4. The device of claim 2, wherein the support channel has a length of less than 5 cm.

5. The device of claim 2, wherein the support channel has a wedge-shaped leading edge.

6. The device of claim 1, wherein the spreader mechanism comprises a gear box and a device for turning the gear box.

7. The device of claim 6, wherein the gear box comprises a first gear segment secured to at least one of the first and second generally U-shaped actuator members and a gear wheel to engage the first gear segment.

8. The device of claim 7, wherein the gear box further comprises a second gear segment secured to a second actuator member.

9. The device of claim 1, further comprising a mount configured to secure the device to an operating table.

10. A device for expanding an opening formed below a skin layer of a patient, the opening having opposite sides, the device comprising:
    a first arm for engaging one side of the opening;
    a second arm for engaging the other side of the opening, wherein the first arm overlays the second arm in a vertical plane;
    a first actuator member connected to the first arm;
    a second actuator member connected to the second arm; and
    a spreader mechanism, coupled to at least one of the first and second actuator members, to move the arms apart in a horizontal plane, wherein the arms are adapted to move between a retracted position in which the arms are positioned next to one another and an extended position in which the arms are extended to expand the opening.

11. The device of claim 10, wherein each of the first arm and the second arm comprises a distracter shaft, and a support channel releasably secured to the distracter shaft, the support channel being configured to engage a side of the opening below the skin layer.

12. The device of claim 11, wherein the support channel has a length of less than 5 cm.

13. The device of claim 11, wherein the support channel includes a C-shaped surface that is configured to engage a divided breastbone of the patient below the skin layer.

14. The device of claim 11, wherein the spreader mechanism comprises a gear box and a device for turning the gear box.

15. The device of claim 14, wherein the gear box comprises a first gear segment secured to at least one of the actuator members and a gear wheel to engage the first gear segment.

16. The device of claim 15, wherein the gear box further comprises a second gear segment secured to the second actuator member.

17. The device of claim 14, further comprising a mount configured to secure the device to an operating table.

18. A device for expanding an opening formed below a skin layer of a patient, the opening having opposite sides, the device comprising:

a first arm for engaging one side of the opening;

a second arm for engaging the other side of the opening;

a first actuator member connected to the first arm;

a second actuator member connected to the second arm;

wherein one actuator member is configured to overlay the other actuator member in a vertical plane;

a spreader mechanism, coupled to at least one of the first and second actuator members, to move the arms apart in a horizontal plane, wherein the arms are adapted to move between a retracted position in which the arms are positioned next to one another and an extended position in which the arms are extended to expand the opening.

19. The device of claim 18, wherein each of the first arm and the second arm comprises a distracter shaft, and a support channel releasably secured to the distracter shaft, the support channel being configured to engage a side of the opening below the skin layer.

20. The device of claim 19, wherein the support channel includes a C-shaped surface that is configured to engage a divided breastbone of the patient below the skin layer.

* * * * *